(12) United States Patent
Ramsay et al.

(10) Patent No.: US 9,855,077 B2
(45) Date of Patent: *Jan. 2, 2018

(54) SPINAL IMPLANT WITH A FLEXIBLE EXTENSION ELEMENT

(71) Applicant: DEPUY SYNTHES PRODUCTS, INC., Raynham, MA (US)

(72) Inventors: Christopher L. Ramsay, West Wareham, MA (US); Sara Dziedzic, North Attleboro, MA (US); Michael Mahoney, Middletown, RI (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,272

(22) Filed: Jun. 6, 2016

(65) Prior Publication Data

US 2016/0278816 A1 Sep. 29, 2016

Related U.S. Application Data

(60) Continuation of application No. 13/541,069, filed on Jul. 3, 2012, now Pat. No. 9,364,265, which is a
(Continued)

(51) Int. Cl.
*A61B 17/70* (2006.01)
*A61B 17/00* (2006.01)
(Continued)

(52) U.S. Cl.
CPC ...... *A61B 17/7037* (2013.01); *A61B 17/7032* (2013.01); *A61B 17/7053* (2013.01);
(Continued)

(58) Field of Classification Search
CPC ............ A61B 17/7085; A61B 17/8038; A61B 17/7032
See application file for complete search history.

(56) References Cited

U.S. PATENT DOCUMENTS

| 4,805,602 A | 2/1989 | Puno et al. |
| 5,242,446 A | 9/1993 | Steffee et al. |

(Continued)

FOREIGN PATENT DOCUMENTS

| EP | 1374786 A2 | 1/2004 |
| EP | 1449486 A1 | 8/2004 |

(Continued)

OTHER PUBLICATIONS

U.S. Appl. No. 13/541,069, filed Jul. 3, 2012, Christopher L. Ramsay.

(Continued)

*Primary Examiner* — Jan Christopher Merene
*Assistant Examiner* — Atiya Mahmud
(74) *Attorney, Agent, or Firm* — Nelson Mullins Riley & Scarborough LLP

(57) ABSTRACT

A spinal implant with at least one flexible elongated extension element is provided. The spinal implant has a profile that is lower than standard spinal implants. The spinal implant includes a bone anchor with a head portion and a shaft extending along a longitudinal axis of the bone anchor. A head plate is coupled to the bone anchor. The head plate includes a first elongated extension element and a second elongated extension element. The first elongated extension element and the second elongated extension element may be formed as a single monolithic element that is attached to the head plate by passing through a pair of openings provided on the head plate. At least one of the first elongated extension element and the second elongated extension element is flexible.

2 Claims, 17 Drawing Sheets

Related U.S. Application Data division of application No. 12/582,517, filed on Oct. 20, 2009, now Pat. No. 8,236,032.

(51) Int. Cl.
*A61B 90/00* (2016.01)
*A61B 17/56* (2006.01)
*A61B 17/68* (2006.01)

(52) U.S. Cl.
CPC ... *A61B 17/7076* (2013.01); *A61B 2017/00867* (2013.01); *A61B 2017/567* (2013.01); *A61B 2017/681* (2013.01); *A61B 2090/037* (2016.02)

(56) References Cited

U.S. PATENT DOCUMENTS

| | | |
|---|---|---|
| 5,360,431 A | 11/1994 | Puno et al. |
| 5,624,442 A | 4/1997 | Mellinger et al. |
| 5,634,932 A | 6/1997 | Schmidt |
| 5,910,141 A | 6/1999 | Morrison et al. |
| 6,183,472 B1 | 2/2001 | Lutz |
| 6,299,616 B1 | 10/2001 | Beger |
| 6,325,802 B1 | 12/2001 | Frigg |
| 6,355,039 B1 | 3/2002 | Troussel et al. |
| 6,443,955 B1 | 9/2002 | Ahrend et al. |
| 6,458,132 B2 | 10/2002 | Choi |
| 6,648,888 B1 | 11/2003 | Shluzas |
| 6,660,006 B2 | 12/2003 | Markworth et al. |
| 6,740,086 B2 | 5/2004 | Richelsoph |
| 6,743,231 B1 | 6/2004 | Gray |
| 6,790,209 B2 | 9/2004 | Beale et al. |
| 6,793,657 B2 | 9/2004 | Lee et al. |
| 7,156,849 B2 | 1/2007 | Dunbar et al. |
| 7,160,300 B2 | 1/2007 | Jackson |
| 7,278,995 B2 | 10/2007 | Nichols et al. |
| 7,846,093 B2 | 12/2010 | Gorek et al. |
| 8,097,026 B2 | 1/2012 | Gorek |
| 8,236,032 B2 | 8/2012 | Ramsay et al. |
| 8,556,940 B2 | 10/2013 | Hua |
| 8,696,560 B2 | 4/2014 | Strauss et al. |
| 9,364,265 B2 | 6/2016 | Ramsay |
| 2002/0138077 A1 | 9/2002 | Ferree |
| 2004/0049191 A1 | 3/2004 | Markworth et al. |
| 2004/0147937 A1 | 7/2004 | Dunbar et al. |
| 2005/0033299 A1 | 2/2005 | Shluzas |
| 2005/0131421 A1 | 6/2005 | Anderson et al. |
| 2005/0131422 A1 | 6/2005 | Anderson et al. |
| 2005/0177154 A1 | 8/2005 | Moumene et al. |
| 2005/0192570 A1 | 9/2005 | Jackson |
| 2005/0192589 A1 | 9/2005 | Raymond et al. |
| 2005/0215999 A1 | 9/2005 | Birkmeyer et al. |
| 2005/0277927 A1* | 12/2005 | Guenther ............ A61B 17/7037 606/308 |
| 2006/0025771 A1 | 2/2006 | Jackson |
| 2006/0058794 A1 | 3/2006 | Jackson |
| 2006/0111712 A1 | 5/2006 | Jackson |
| 2006/0111713 A1 | 5/2006 | Jackson |
| 2006/0184178 A1 | 8/2006 | Jackson |
| 2006/0247658 A1 | 11/2006 | Pond et al. |
| 2006/0293680 A1 | 12/2006 | Jackson |
| 2007/0073294 A1 | 3/2007 | Chin et al. |
| 2007/0106123 A1 | 5/2007 | Gorek et al. |
| 2007/0161998 A1 | 7/2007 | Whipple |
| 2007/0233079 A1 | 10/2007 | Fallin et al. |
| 2007/0233097 A1 | 10/2007 | Anderson et al. |
| 2008/0051789 A1 | 2/2008 | Snyder et al. |
| 2008/0051794 A1 | 2/2008 | Dec et al. |
| 2008/0161857 A1 | 7/2008 | Hestad et al. |
| 2008/0221621 A1 | 9/2008 | Snyder et al. |
| 2008/0262318 A1 | 10/2008 | Gorek et al. |
| 2009/0131755 A1 | 5/2009 | White et al. |
| 2009/0221878 A1 | 9/2009 | Gorek |
| 2009/0221879 A1 | 9/2009 | Gorek |
| 2009/0222044 A1 | 9/2009 | Gorek |
| 2009/0222045 A1 | 9/2009 | Gorek |
| 2009/0222046 A1 | 9/2009 | Gorek |
| 2009/0248082 A1 | 10/2009 | Crook et al. |
| 2010/0292739 A1* | 11/2010 | Schwab ............ A61B 17/7032 606/305 |
| 2011/0054259 A1 | 3/2011 | Gorek et al. |
| 2011/0087293 A1 | 4/2011 | Ferreira et al. |
| 2011/0209821 A1 | 9/2011 | Gorek |

FOREIGN PATENT DOCUMENTS

| | | |
|---|---|---|
| FR | 2801492 A1 | 6/2001 |
| WO | 08/039247 A2 | 4/2008 |

OTHER PUBLICATIONS

U.S. Appl. No. 12/582,517, filed Oct. 20, 2009, Christopher L. Ramsay.
Australian Office Action for Application No. 19915/U9858/CDM/dh, 4 pages, dated May 21, 2014.
Chinese Office Action for Application No. 201080058302.4, 6 pages, dated Mar. 4, 2014.
European Examination Report, European Application No. 10825571.2, dated Aug. 28, 2015, pp. 1-5.
Extended European Search Report issued in European Patent Application No. 10825571.2 dated Oct. 17, 2014.
International Search Report for Application No. PCT/US2010/053331, 2 pages, dated Dec. 10, 2010.
Japanese Office Action for Application No. 2012-535327, dated Apr. 15, 2014, 5 pages.

* cited by examiner

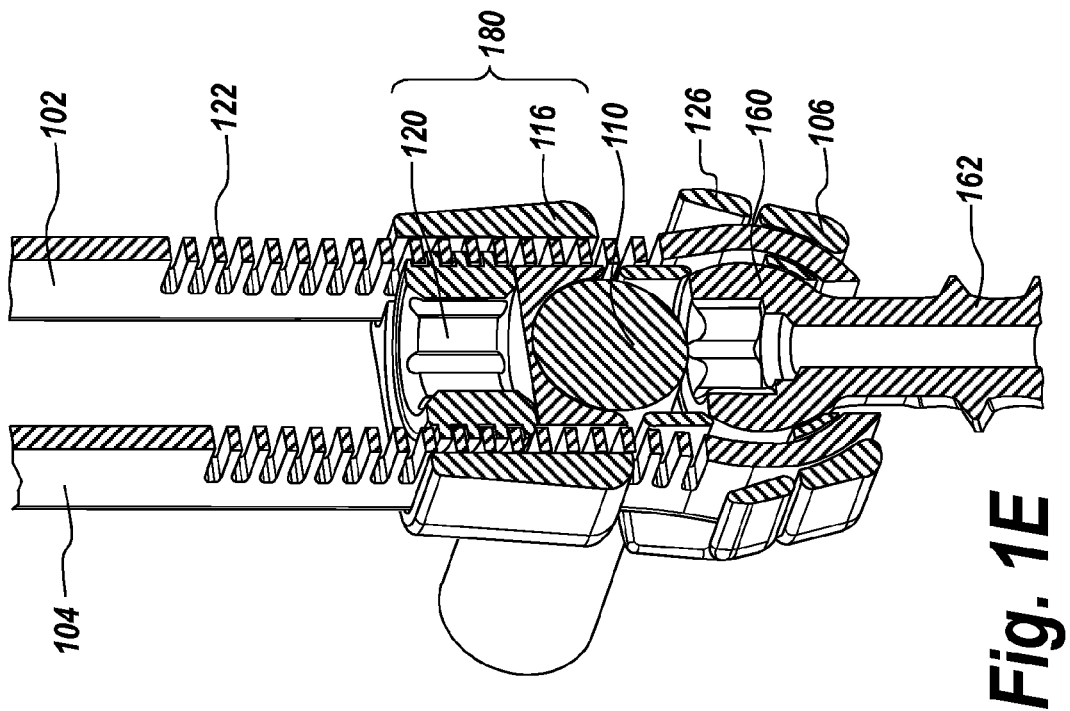
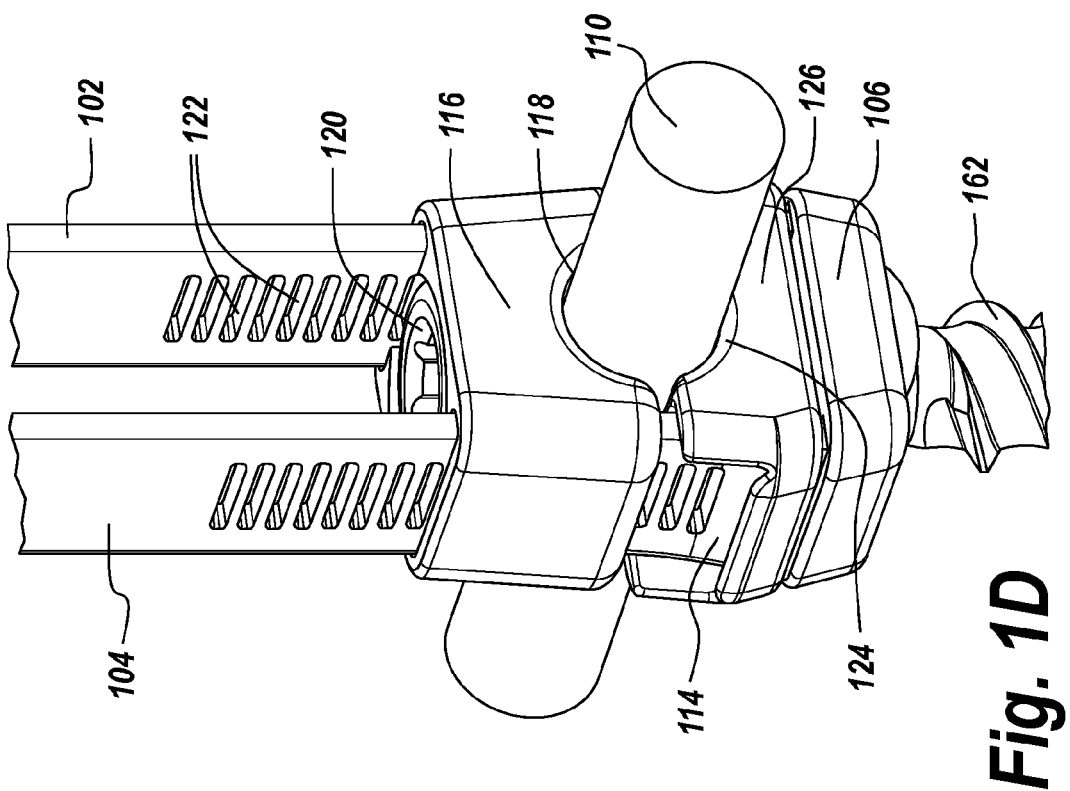

SPINAL IMPLANT WITH A FLEXIBLE EXTENSION ELEMENT

RELATED APPLICATIONS

This application is a continuation of U.S. patent application Ser. No. 13/541,069, filed on Jul. 3, 2012, which is a divisional application of U.S. patent application Ser. No. 12/582,517, filed Oct. 20, 2009, now U.S. Pat. No. 8,236,032, the contents of which are hereby incorporated by reference.

FIELD OF THE INVENTION

The present invention relates to spinal connection devices used in orthopedic surgery. More particularly, the present invention relates to a spinal implant with at least one flexible elongated extension element.

BACKGROUND OF THE INVENTION

Spinal fixation systems may be used in surgery to align, adjust and/or fix portions of the spinal column, i.e., vertebrae, in a desired spatial relationship relative to each other. Many spinal fixation systems employ a spinal rod, i.e. a spinal fixation element, for supporting the spine and for properly positioning components of the spine for various treatment purposes. The fixation system components, such as vertebral anchors, comprising pins, bolts, screws, and hooks, engage the vertebrae and connect the supporting rod to different vertebrae. The spinal fixation system components can have a predetermined contour that has been designed according to the properties of the target implantation site. Once installed, the spinal fixation system holds the vertebrae in a desired spatial relationship, either until desired healing or spinal fusion has taken place, or for some longer period of time. The size, length and shape of the spinal rod depend on the size, number and position of the vertebrae to be held in a desired spatial relationship relative to each other by the apparatus.

Spinal fixation system components can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shaft that is adapted to be threaded into a vertebra, and a head portion having a spinal fixation element-receiving portion for receiving, for example, a spinal fixation rod. A set-screw, plug, cap or similar type of closure mechanism is used to lock the spinal rod onto the rod-receiving portion of the pedicle screw. In use, the shaft portion of each screw is threaded into a vertebra, and once properly positioned, the spinal fixation rod is seated through the rod-receiving portion of each screw.

Recently, the trend in spinal surgery has been moving toward providing minimally invasive elements and methods for implanting spinal fixation systems. In some anchor devices, rigid extension elements are attached to the heads of the anchor devices and extend out of the skin incision. These rigid extension elements may be used to control the head of the anchor device to assist the spinal fixation element in entering into the head of the anchor device. The rigid extension elements limit the entry zone of the spinal fixation element into the head of the bone anchor. Thus the placement of the spinal fixation element into the bone anchor head becomes very challenging. This is especially problematic in extended constructs where multiple vertebral bodies are being fixated.

One or more bone anchors may not be inserted immediately adjacent to the spinal fixation element. Additionally, in many instances one or more vertebrae may be out of alignment such that the one or more vertebrae and the inserted bone anchor are not immediately adjacent to the inserted spinal rod or the bone anchors do not have comparable heights. In these cases, since the spinal fixation rod cannot follow a well aligned path, it becomes challenging or impossible to place the spinal fixation rod though each bone anchor. Specifically, in percutaneous or minimally invasive procedures, it is more difficult to adjust a spinal rod using a technique such as bending to make contact between the spinal rod and the bone anchors. It is also more difficult to move such vertically or laterally displaced vertebrae so that the vertebrae may be coupled to the spinal rod.

Additionally, the current extension elements used in MIS procedures cause other logistical issues for the procedure. Extension elements that crowd the incision area add complexity to the operation. The time required managing assembling the extensions elements and disengaging them may be extensive.

SUMMARY

Embodiments of the present invention may provide a bone anchor having a shaft to engage a bone. The bone anchor may have a head portion that is provided above the bone. The bone anchor may be a poly-axial screw, a mono-axial screw or a uni-screw. A head plate including a first elongated extension element and a second elongated extension element may be coupled to the bone anchor. The first elongated extension element and the second elongated extension element may be formed as a single monolithic element that is coupled to the head plate by passing through a pair of openings provided on the head plate. A head cap may be coupled to the first elongated extension element, the second elongated extension element and the head plate. A spinal fixation element may be placed on the head cap and stabilized between the head cap and a locking cap. At least one of the elongated extension elements is flexible. As used herein, flexible refers to elements that are capable of being bent, flexed or twisted without unintentionally breaking.

The locking cap may slide along at least one of the elongated extension elements. The locking cap may be lowered toward the head cap to stabilize the spinal fixation element therebetween using the elongated extension elements. Alternatively, the locking cap may be lowered toward the head cap using a set screw. The set screw may be coupled to the locking cap. The elongated extension elements keep some of the soft tissue around the surgical site away from the surgical site to provide clearance for the spinal fixation element. Thus, the surgeon may have better access to the surgical site and may controllably implant the spinal fixation element. The elongated extension elements may stick out of the surgical site. A portion of the elongated extension elements is removed upon placing the spinal fixation element in a desired position.

According to a first aspect of the invention a spinal implant is provided. The spinal implant includes a bone anchor, a head plate and a head cap. The bone anchor has a head portion positioned above a bone and a shaft that extends along a longitudinal axis of the bone anchor. The shaft is configured to engage a bone. The head plate is coupled to the bone anchor. The head plate includes a first elongated extension element and a second elongated extension element. The first elongated extension element may be flexible. The first elongated element is provided on a first side of the head plate. The second elongated extension element is provided on a second side, across from the first side, of the head plate. The first elongated extension element and the second elongated extension element may be provided as a single monolithic element that passes through a pair of openings provided on each side of the head plate. The head cap is coupled to the head plate, the first elongated extension element and the second elongated extension element. The spinal fixation element is positioned on a seat portion of the head cap provided between the first elongated extension element and the second elongated extension element.

According to various aspects of the present invention, the spinal implant may also include an anchor locking cap adapted to move along at least one of the first elongated extension element and the second elongated extension element. The anchor locking cap is adapted to fit over the spinal fixation element so as to stabilize the spinal fixation element between the seat portion of the head cap and the anchor locking cap.

According to other aspects of the present invention, the spinal implant may further include a plurality of reduction features provided on at least one of the first elongated extension element and the second elongated extension element. The plurality of reduction features provide a controlled movement of the anchor head cap along at least one of the first elongated extension element and the second elongated extension element. The controlled movement prevents the anchor head cap from sliding along the first elongated extension element or the second elongated extension element.

According to another aspect of the present invention, a method for placing a spinal fixation element over a bone anchor in a minimally invasive surgery is provided. The bone anchor has a shaft portion configured to be placed in a bone and a head portion configured to stay above the bone. A first elongated extension element and a second elongated extension element are coupled to a head plate by passing the first elongated extension element and the second elongated extension element through a pair of openings provided on the head plate. The bone anchor is coupled to the head plate when the shaft portion of the bone anchor is passed through a central opening provided on the head plate. The shaft portion of the bone anchor is inserted in a bone. The first elongated extension element, the second elongated extension element and the head plate stay above the bone. A head cap is coupled to the first elongated extension element, the second elongated extension element and the head plate. The first elongated extension element and second elongated extension element pass through a pair of openings provided on the head cap. The spinal fixation element is placed over a seat portion provided on the head cap through a passage formed by the first elongated extension element and the second elongated extension element. A locking cap is placed over at least one of the first elongated extension element and the second elongated extension element. The locking cap is reduced along the at least one of the first elongated extension element and the second elongated extension element. The spinal fixation element is stabilized between the head cap and the locking cap.

According to various aspects, the method may also include removing a portion of the first extension element and/or the second extension element. The locking cap may be lowered using the first elongated extension element and the second elongated extension element. The spinal fixation element may be provided at a distance above the seat portion of the head cap. The locking cap stabilizes the spinal fixation element in place. The first elongated extension element and the second elongated extension element may be flexible.

According to another aspect, the first elongated extension element is flexible and the second elongated extension element is substantially rigid. In this exemplary embodiment, the first elongated extension element may be placed through an opening provided on the second elongated extension element so as to form a loop around the spinal fixation element. The locking cap locks to the head cap so as to enclose the spinal fixation element and a portion of the first elongated extension element forming the loop.

According to yet another aspect, a spinal implant is provided. The spinal implant includes a head portion, a shaft and a head plate. The head portion is provided above a bone. The shaft is configured to engage the bone. The head plate is coupled to the head portion and the shaft. The head plate includes a pair of extension sleeves for expanding an engagement area of a spinal fixation element with the head plate. At least one of the pair of extension sleeves is flexible. The pair of extension sleeves has a shaped distal end providing a wider opening for the spinal fixation element than a surface of the head plate.

BRIEF DESCRIPTION OF THE FIGURES

The foregoing and other objects, features and advantages of the invention will be apparent from the following description and apparent from the accompanying drawings. The drawings illustrate principles of the invention and, although not to scale, show relative dimensions.

FIGS. 1C-1F illustrate a closure mechanism of the exemplary spinal implant of FIG. 1A stabilizing a spinal fixation element;

DETAILED DESCRIPTION OF THE INVENTION

Figure 1A:
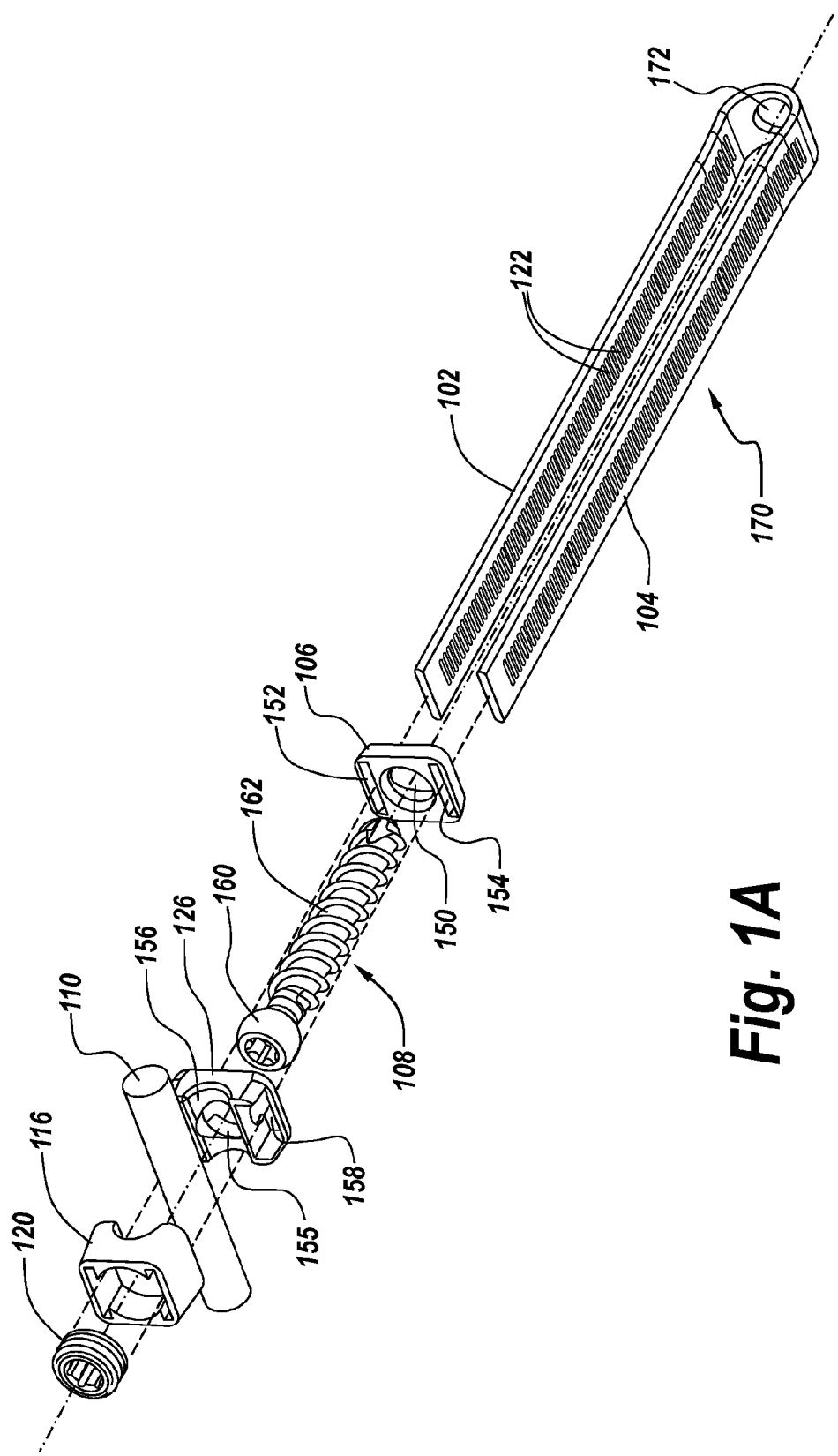
FIG. 1A illustrates how elements forming an exemplary spinal implant couple together.

Embodiments of the present invention may provide an improved spinal implant with a profile that is lower than standard spinal implants to be used in minimally invasive surgeries. The spinal implant may include at least one flexible elongated extension element. The spinal implant may allow for controlled placement of a spinal fixation element. One skilled in the art will recognize that the invention is not limited to use in bone or in spinal surgery, and that the spinal implant and methods described herein can be adapted for use with any suitable surgical device to be moved into a selected position in a variety of medical procedures.

FIGS. 1A-1F illustrate an exemplary spinal implant 100. The spinal implant 100 includes a poly-axial or mono-axial screw 108. The screw 108 includes a head portion 160 and a shaft 162 extending away from the head portion 160 along a longitudinal axis of the screw 108. The shaft 162 of the screw 108 engages a bone while the head portion 160 of the screw 108 stays above the bone. According to various embodiments of the present invention, the screw 108 may be a uni-screw. The exemplary spinal implant 100 further includes a head plate 106. The shaft 182 of the screw 108 passes through a central opening 150 of the head plate 106 such that the head portion 160 stays on a first side of the head plate 106 and the shaft 162 stays on a second side, opposite to the first side, of the head plate 106. The head plate 106 also includes a first opening 152 and a second opening 154 provided on each side of the central opening 150. The exemplary spinal implant 100 also includes a first elongated extension element 102 and a second elongated extension element 104. The first elongated extension element 102 may pass through the first opening 152 of the head plate 106 and the second extension element 104 may pass through the second opening 154 of the head plate 106. Alternatively, the first elongated extension element 102 and the second elongated extension element 104 may be attached to or formed integrally with the head plate 106.

According to the various embodiments of the present invention, the first elongated extension element 102 and the second elongated extension element 104 may be formed as a single monolithic element by bending a single extension element 170. The single extension element 170 may have a central opening 172 at the bent portion provided at the distal end thereof. The shaft 162 of the screw 108 may pass through the central opening 172 of the single extension element 170 when the spinal implant 100 is assembled as illustrated in FIG. 1A.

The exemplary spinal implant 100 illustrated in FIG. 1A further includes a head cap 126 that is coupled to the head plate 106. The head cap 126 may be coupled to the head plate 106 by means of the first elongated extension element 102 and the second elongated extension element 104. The head cap 126 may also be coupled to the head plate 106 by compress fitting, welding or any other feasible means. The head cap 126 may include a central opening 150 to accommodate the head portion 160 of the screw 108. The head portion 160 of the screw 108 may fit into the central opening 155 of the head cap 126. The head cap 126 may also include a first opening 156 and a second opening 158 provided on each side of the central opening 155. The first opening 156 and the second opening 158 of the head cap 126 may be aligned with the first opening 152 and the second opening 154 of the head plate 106, respectively. The first elongated extension element 102 may pass through the first opening 156 of the head cap 126 and the second elongated extension element 104 may pass through the second opening 158 of the head cap 126 to couple the head cap 126 to the head plate 106. According to various embodiments of the present invention, the head cap 126 may be formed integrally with the head plate 106 of the exemplary spinal implant 100.

Figure 1B:
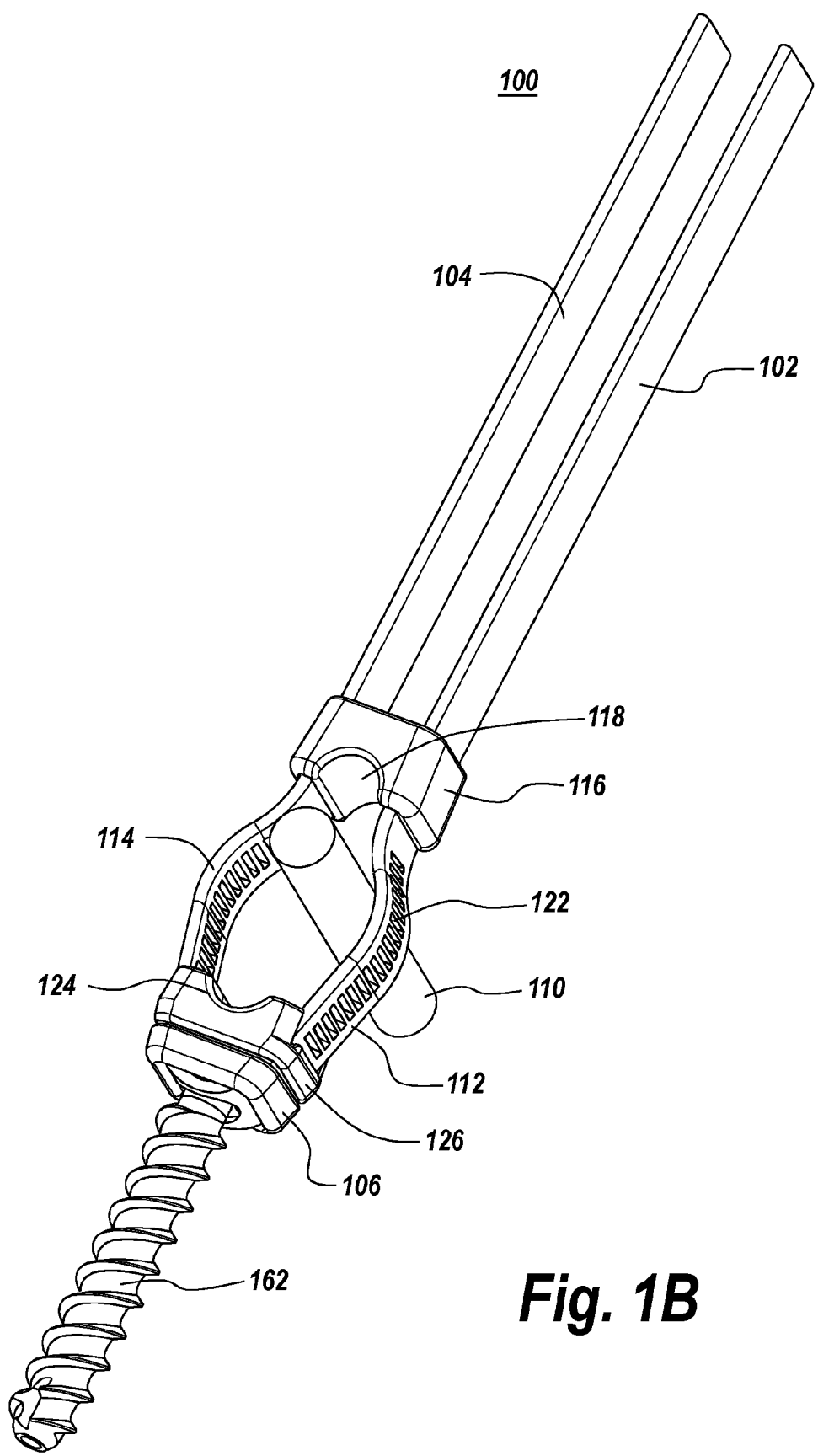
FIG. 1B illustrates elongated extension elements of the exemplary spinal implant of FIG. 1A having a biased distal geometry.
Figure 1C:
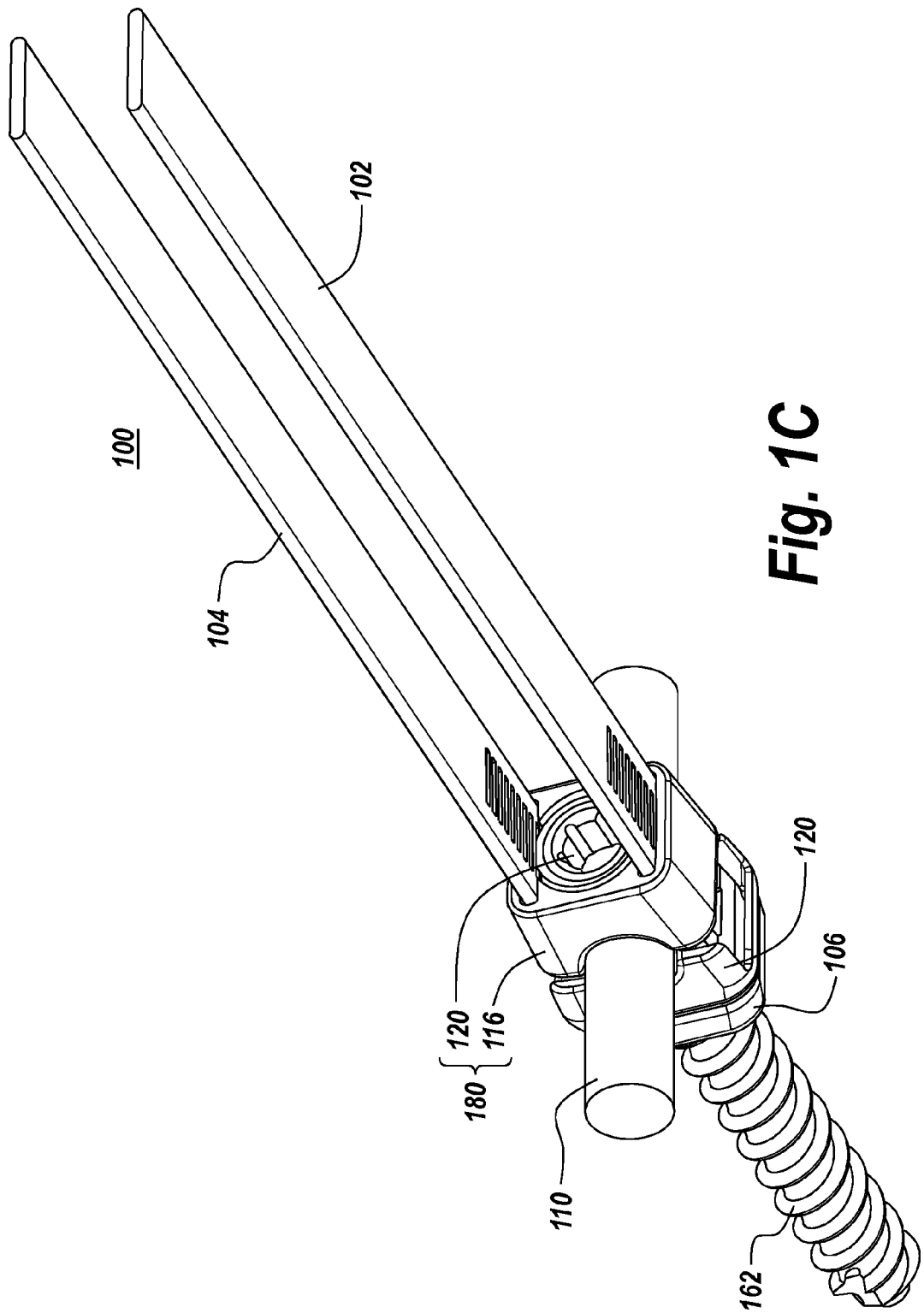

As illustrated in FIG. 1B, a distal end of the first elongated extension element 112 and a distal end of the second elongated extension element 114 may have a biased geometry at a location closer to the head cap 126. A distance between the distal end of the first elongated extension element 112 and the distal end of the second elongated extension element 114 may form a larger opening than the surface of the head plate 106. The biased distal geometry may be formed by providing a curve at the distal ends 112 and 114 of the first elongated extension element 102 and the second elongated extension element 104, respectively. The curve is formed by each elongated extension element curving outward, away from the other elongated extension element at the distal end thereof. The biased distal geometry allows a horizontal movement of the spinal fixation element 110 for easier placement and placement correction of the spinal fixation element 110. The biased distal geometry may be eliminated by placing a locking cap 116 over the distal ends of the elongated extension elements 112 and 114. When the biased distal geometry, i.e. the curve, is eliminated, the elongated extension elements 102 and 104 no longer have the curved shaped at their respective distal ends, 112 and 114. Alternatively, the biased geometry may be eliminated by using a secondary tool.

The biased distal geometry may be formed during manufacturing of the elongated extension elements 102 and 104. The elongated extension elements 102 and 104 may be made of biocompatible shape memory alloy, such as nitinol. The elongated extension elements 102 and 104 may be bent and shaped to acquire a desired form that provides a larger horizontal opening between the distal ends 112 and 114 of the elongated extension elements 102 and 104, respectively. The horizontal opening at the biased distal geometry may be larger than the opening at the proximal ends of the elongated extension elements 102 and 104.

FIGS. 1C-1F illustrate the closure mechanism 180 according to an exemplary embodiment of the spinal implant 100. The closure mechanism 180 may include a locking cap 116 and a set screw 120. The locking cap 116 is provided around one or both of the elongated extension elements 102 and 104. The locking cap 116 slides along the first elongated extension element 102 and/or the second elongated extension element 104 to stabilize the spinal fixation element 110 in place. Alternatively, the locking cap 116 may be driven toward the head cap 126 by the set screw 120 along the first elongated extension element 102 and/or the second elongated extension element 104 to stabilize the spinal fixation element 110 on a seat portion 124 of the head cap 126.

According to various embodiments of the present invention, the set screw 120 may fit into the locking cap 116. The set screw 120 may be formed integrally with the locking cap 116 such that the set screw 120 may be free to spin within the locking cap 116 without being able to be detached therefrom. The set screw 120 may further keep the locking cap 116 at a desired position. The set screw 120 may drive the locking cap 116 toward the desired position. The set screw 120 may be set in place using a second tool, such as a screwdriver that mates with the set screw 120. Setting the set screw 120 reduces the spinal fixation element 110 toward the head cap 126 and prevents the locking cap 116 from moving along a vertical direction over the first elongated extension element 102 and the second elongated extension element 104.

According to various embodiments of the present invention, any of the first elongated extension element 102 and the second elongated extension element 104 may have surface features 122 that prevent the locking cap 116 from uncontrollably sliding along the first elongated extension element 102 and/or the second elongated extension element 104. The locking cap 116 may mate with the surface features 122 to increase friction between the locking cap 116 and the elongated extension elements 102 and 104.

Figure 1F:
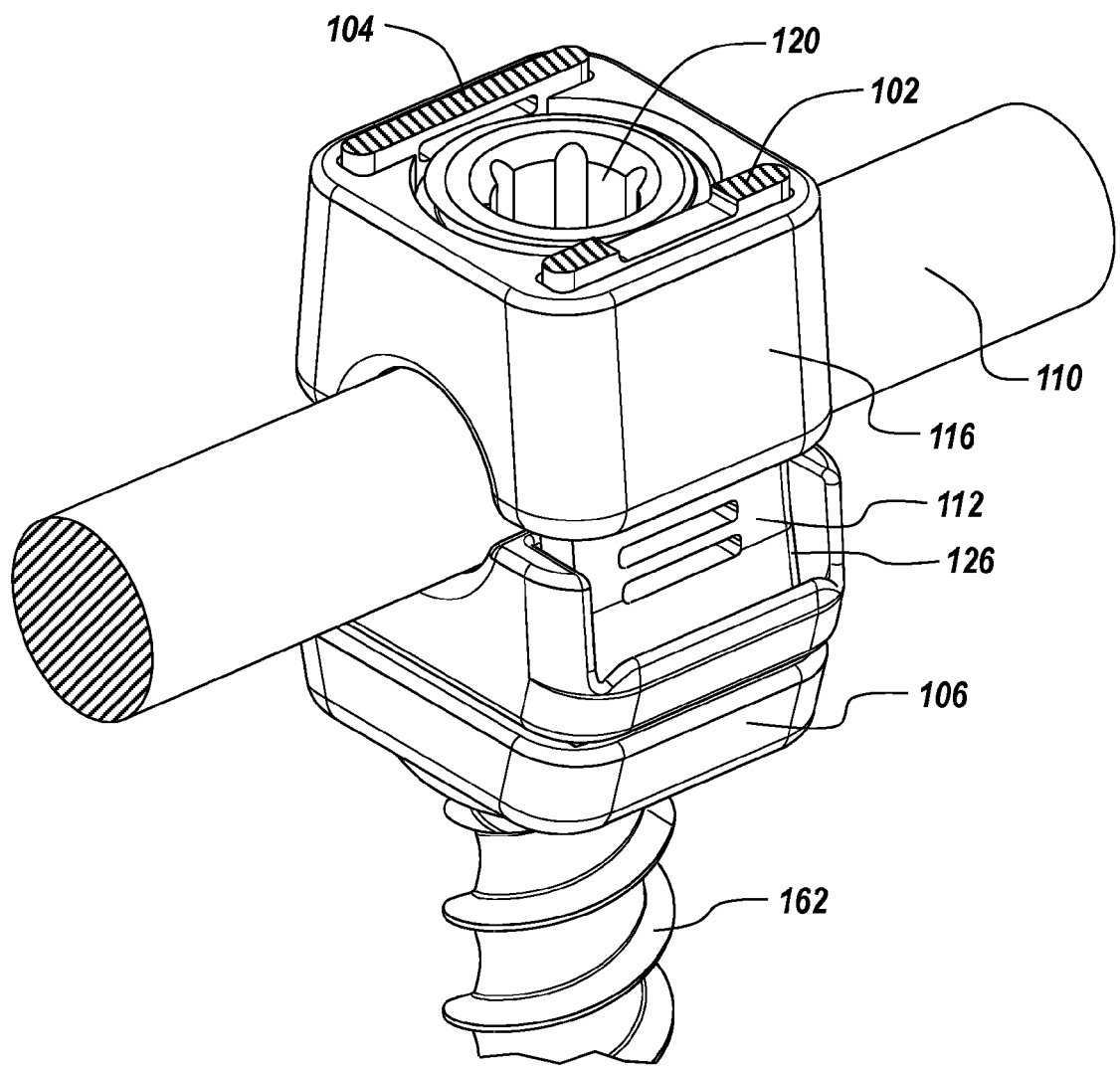

As illustrated in FIGS. 1D-1F, when the locking cap 116 is lowered, the spinal fixation element 110 is held in place between the seat portion 124 of the head cap 126 and the locking cap 116. The surface 118 of the locking cap 116 and the surface of the seat portion 124 facing the spinal fixation element 110 may be shaped to fit the shape of the spinal fixation element 110. For example, if the spinal fixation element 110 is a cylindrical spinal fixation element, the surface 118 of the locking cap 116 and the surface of the seat portion 124 may be a concave surface to accommodate the convex outer surface of the cylindrical spinal fixation element.

When the exemplary embodiment illustrated in FIGS. 1A-1F is used with a polyaxial screw, the head portion 160 of the screw 108 may be held within the head plate 106 and the shaft 162 of the screw 108 may rotate about a central axis of the head plate 106. When a polyaxial screw is used, the set screw 120 pressing the spinal fixation element 110 onto the seat portion 124 may also lock the polyaxial screw so as to restrict the movement of the polyaxial screw within the head plate 106.

Sometimes, the spinal fixation element 110 may not be seated on the seat portion 124 due to spatial constraints. For example, the alignment of the vertebrae or the soft tissue at the surgical site may not allow the spinal fixation element 110 to be lowered all the way to be in physical contact with the seat portion 124. The spinal fixation element 110 may also be kept at a distance from the head cap 126 if the surgeon thinks that the vertebra holding the spinal implant 100 may not handle the force of reducing the spinal fixation element 110 to the seat portion 124 the locking cap set screw 120.

In the exemplary embodiment illustrated in FIGS. 1A-1F, both of the first elongated extension element 102 and the second elongated extension element 104 are flexible. However, according to various embodiments of the present invention, the first elongated extension element 102 may be flexible and the second elongated extension element 104 may be substantially rigid. Providing at least one flexible elongated extension element enables the surgeon to move the soft tissue around the skin incision away from the surgical site. The surgeon may also use the flexible elongated extension element to move the bone anchor, i.e. the screw, or to create a larger pathway for the spinal fixation element. A portion of the elongated extension elements may stay outside of the incision area. The extra portions of the elongated extension elements may be removed by cutting or disengaging the extension elements from the head cap 106 upon completing the surgery.

The spinal implant 100 illustrated in FIGS. 1A-1F is implanted in a patient, under the skin. The first elongated extension element 102 and the second elongated extension element 104 may stick out of the skin incision at the surgery site during the procedure. The portions of the extension elements staying above the skin enable the surgeon to locate the spinal implants for placing the spinal fixation element 110 and/or for placing the closure mechanism, e.g. the locking cap 116 or the set screw 120, over the elongated extension elements 102 and 104. The elongated extension elements 102 and 104 also keep the soft tissue away from the incision site and provide a clear view of the surgical site to the surgeon. The flexible elongated extension elements that stick out of the incision area may be bent to be parallel to the patient's skin to reduce crowding at the surgery site. Furthermore, extra portions of the elongated extension elements 102 and 104 are cut and removed or disengaged above the locking cap 116 that remains implanted in the patient.

FIGS. 2A-2E illustrate an exemplary spinal implant 200 with a press or snap fitting closure mechanism 250. The exemplary spinal implant 200 illustrated in FIGS. 2A-2E has a flexible elongated extension element 302 and a substantially rigid elongated extension element 304. Both elongated extension elements 302 and 304 may be integrally formed with the head plate 306. Alternatively, the elongated extension elements 302 and 304 may be coupled to the head plate 306 via a mechanical connection. According to yet another exemplary embodiment, the substantially rigid elongated extension element 304 may be formed integrally with the head plate 306 and the flexible elongated extension element 302 may be coupled to the head plate 306. According to various embodiments of the present invention, the flexible elongated extension element 302 and the substantially rigid elongated extension element 304 may be provided with surface features 122, such as those illustrated in FIG. 1A, to help reduce a locking cap 316 along the elongated extension elements 302 and 304.

Figure 2A:
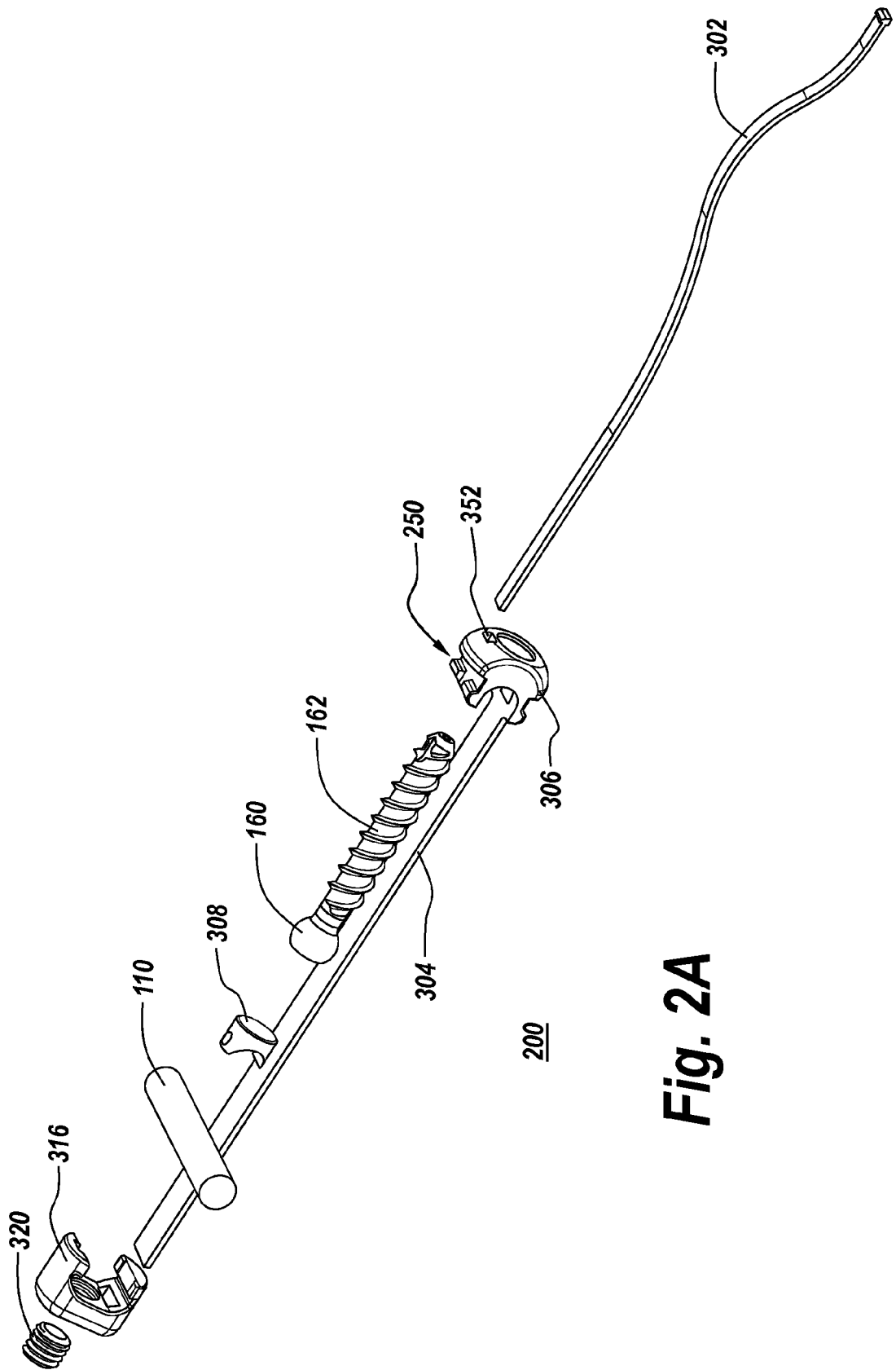
FIG. 2A illustrates how elements forming an exemplary spinal implant having a press fitting closure mechanism couple together.
Figure 2B:
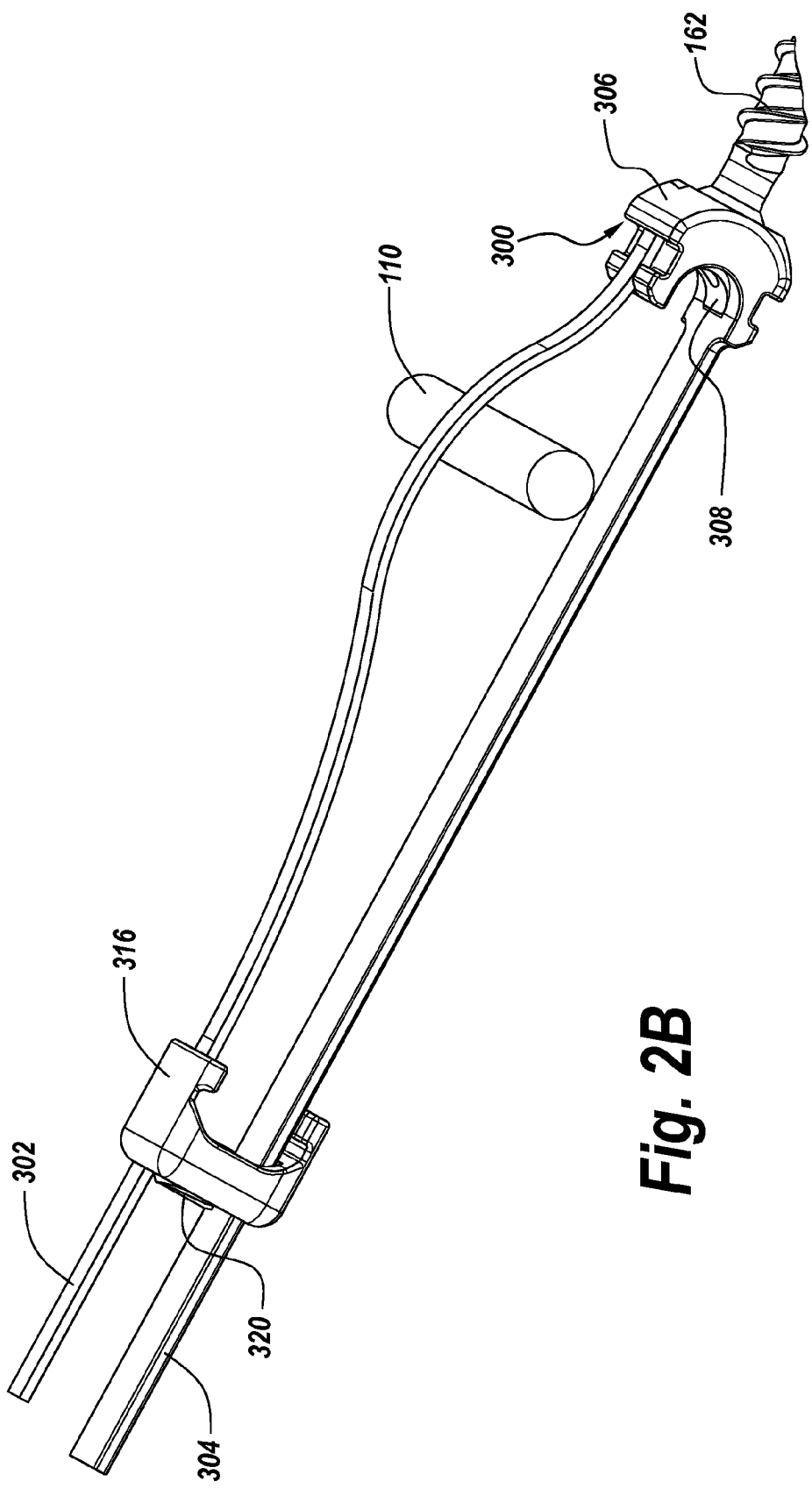
FIG. 2B illustrates an elongated extension element of the exemplary spinal implant of FIG. 2A having a biased distal geometry.
Figures 2C, 2D:
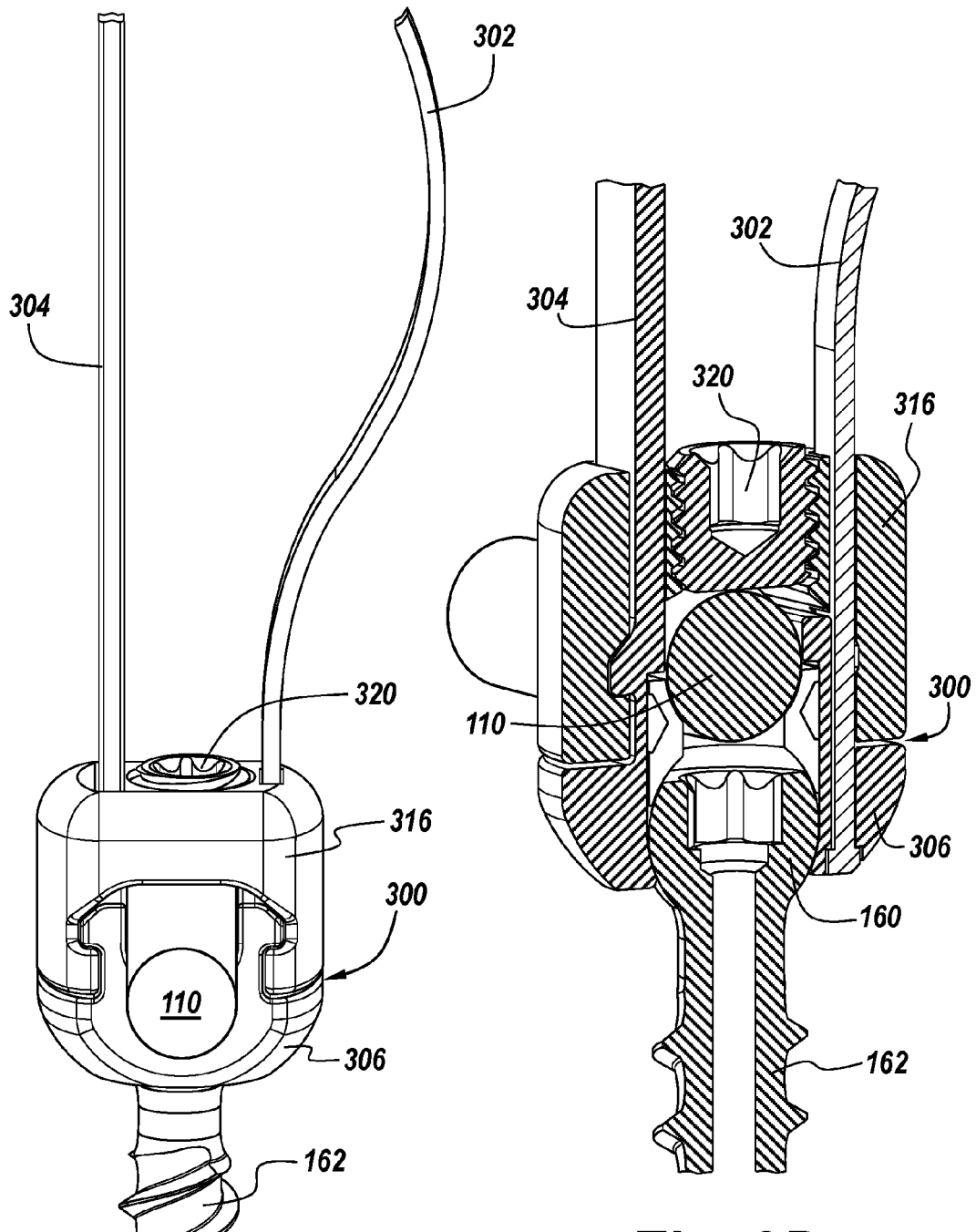
FIGS. 2C-2E illustrate a closure mechanism of the exemplary spinal implant of FIG. 2A stabilizing a spinal fixation element.
Figure 2E:
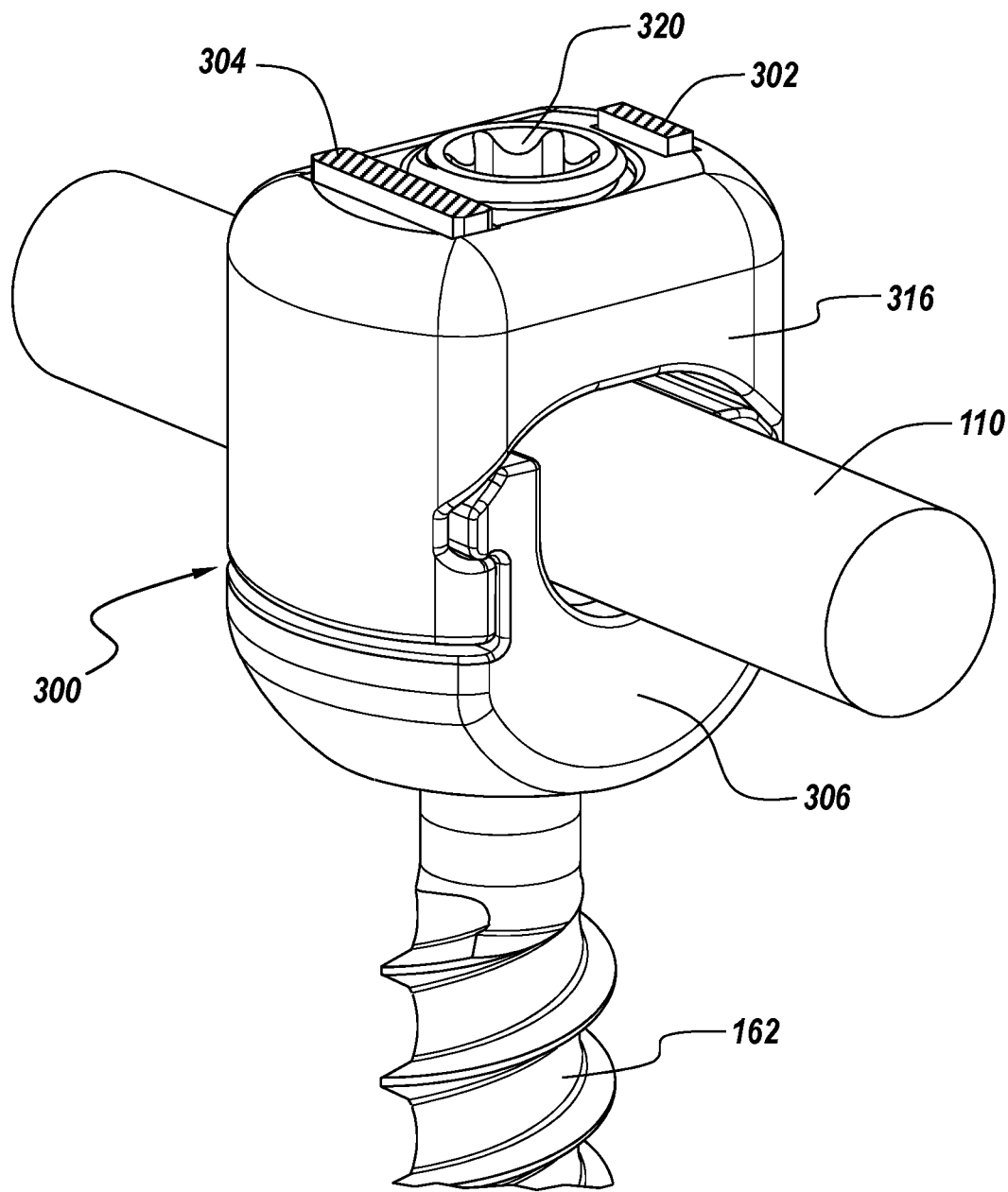
Figure 3A:
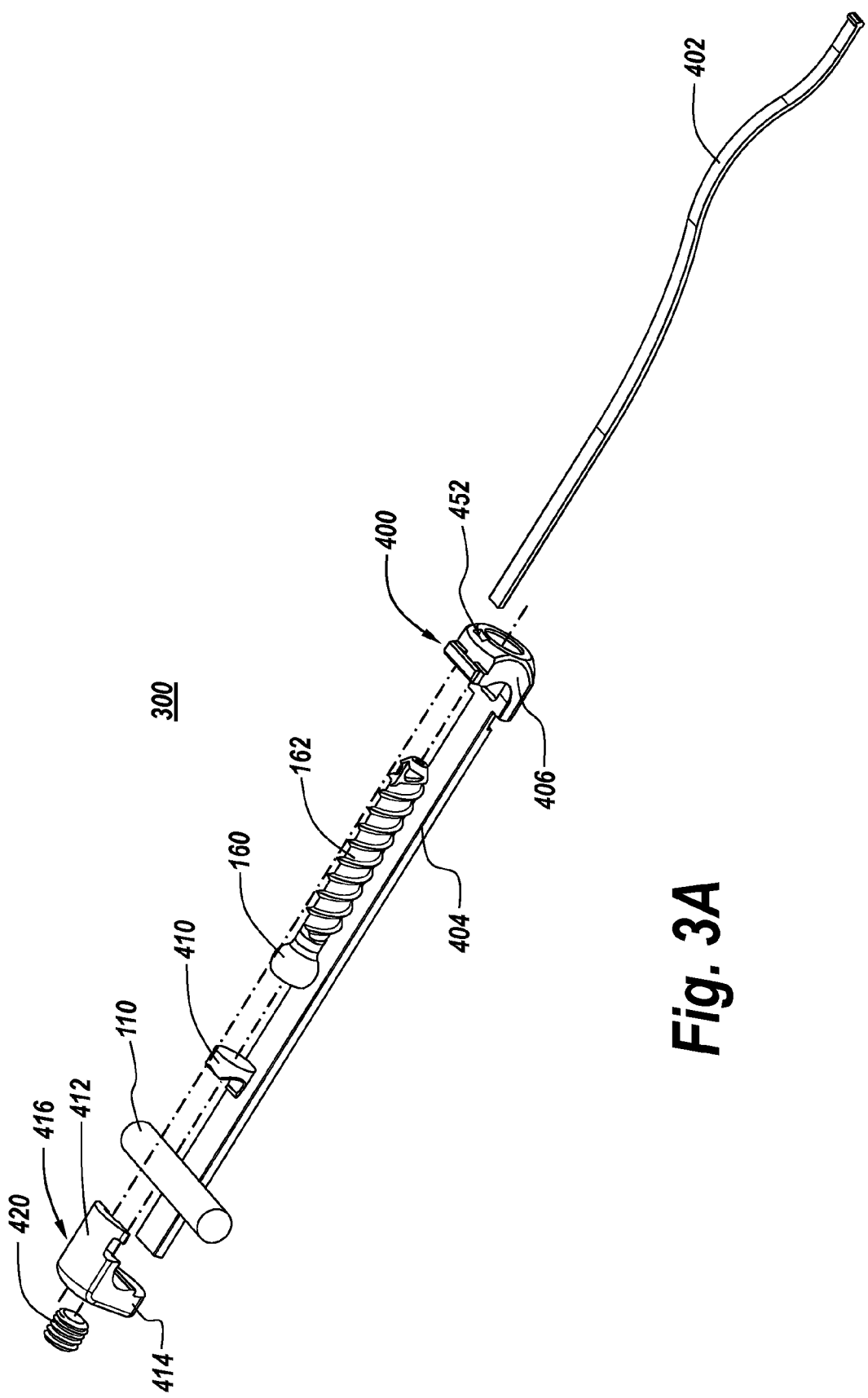
FIG. 3A illustrates how elements forming an exemplary spinal implant having a dovetail closure mechanism couple together.
Figure 3B:
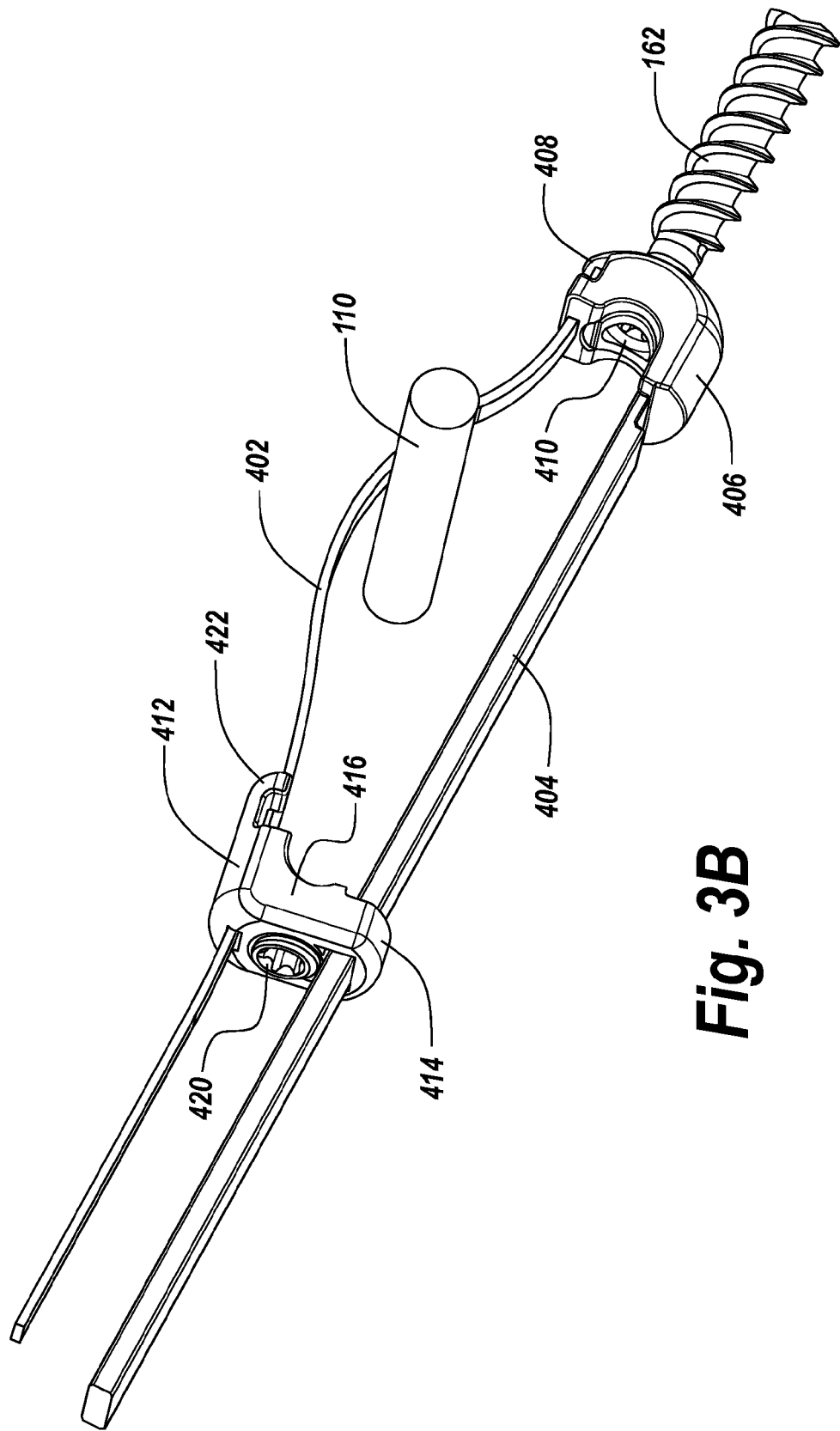
FIG. 3B illustrates an elongated extension element of the exemplary spinal implant of FIG. 3A having a biased distal geometry.
Figure 3C:
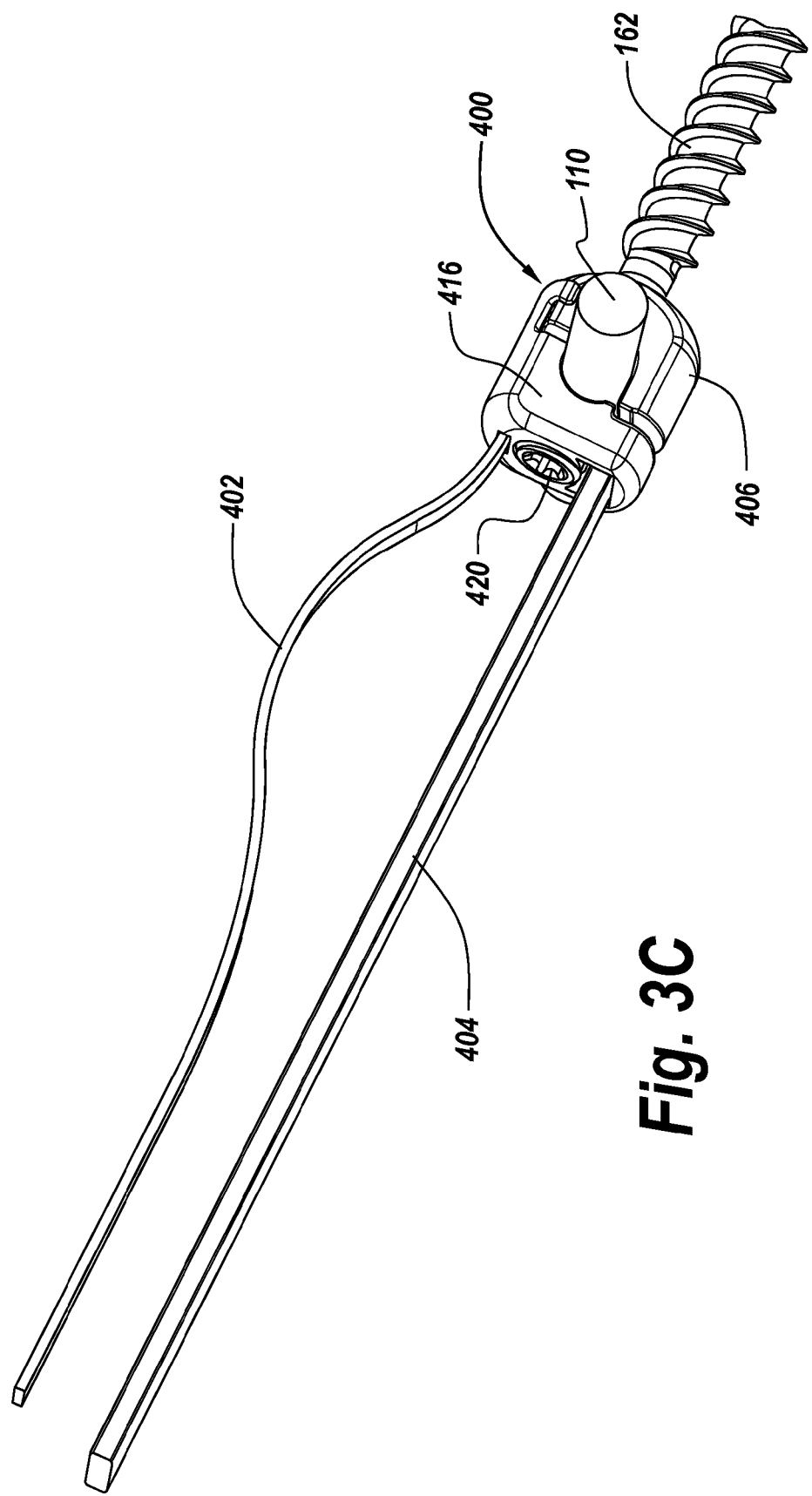
FIGS. 3C-3E illustrate a closure mechanism of the exemplary spinal implant of FIG. 3A stabilizing a spinal fixation element.
Figure 3D:
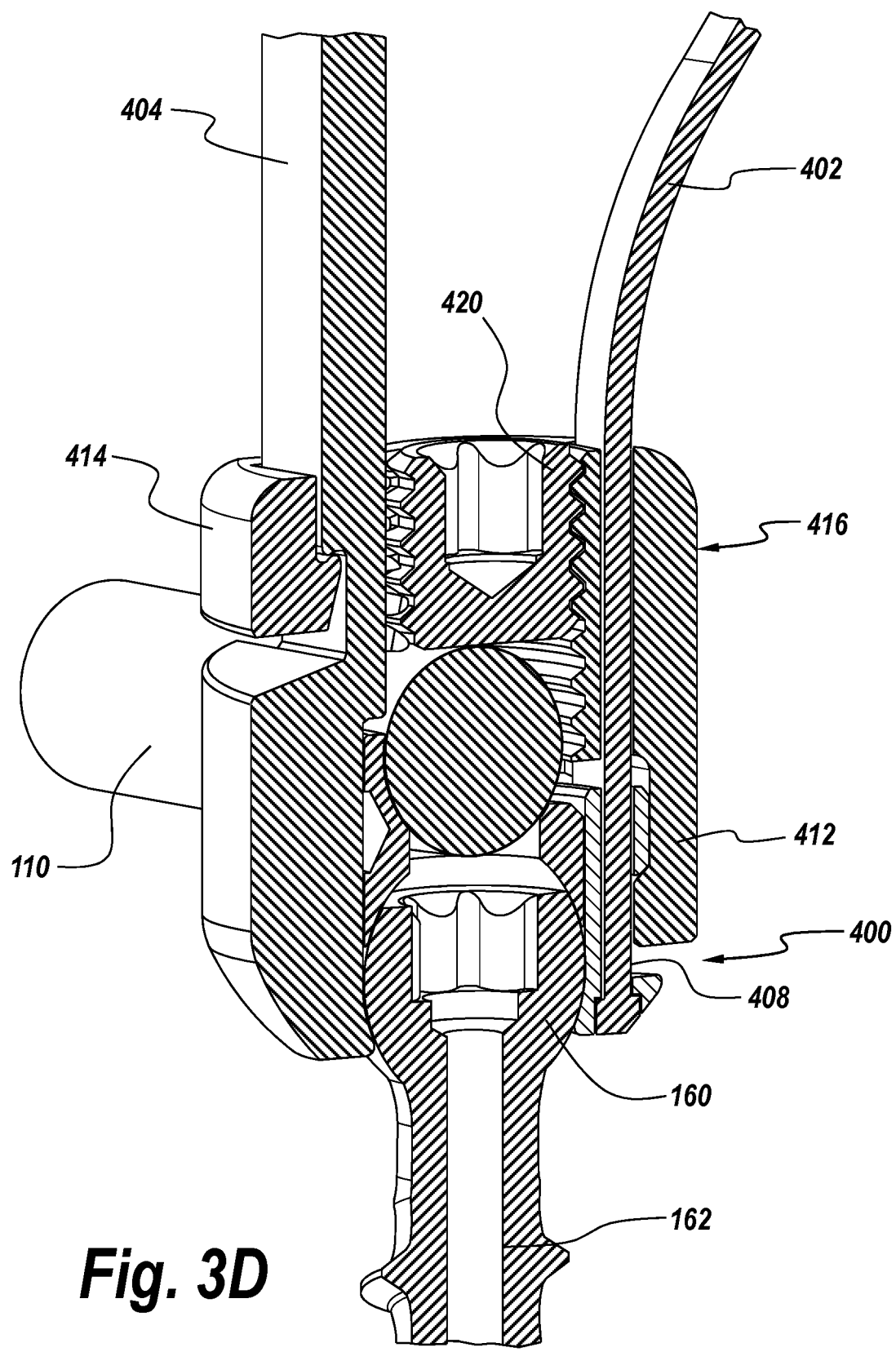
Figure 3E:
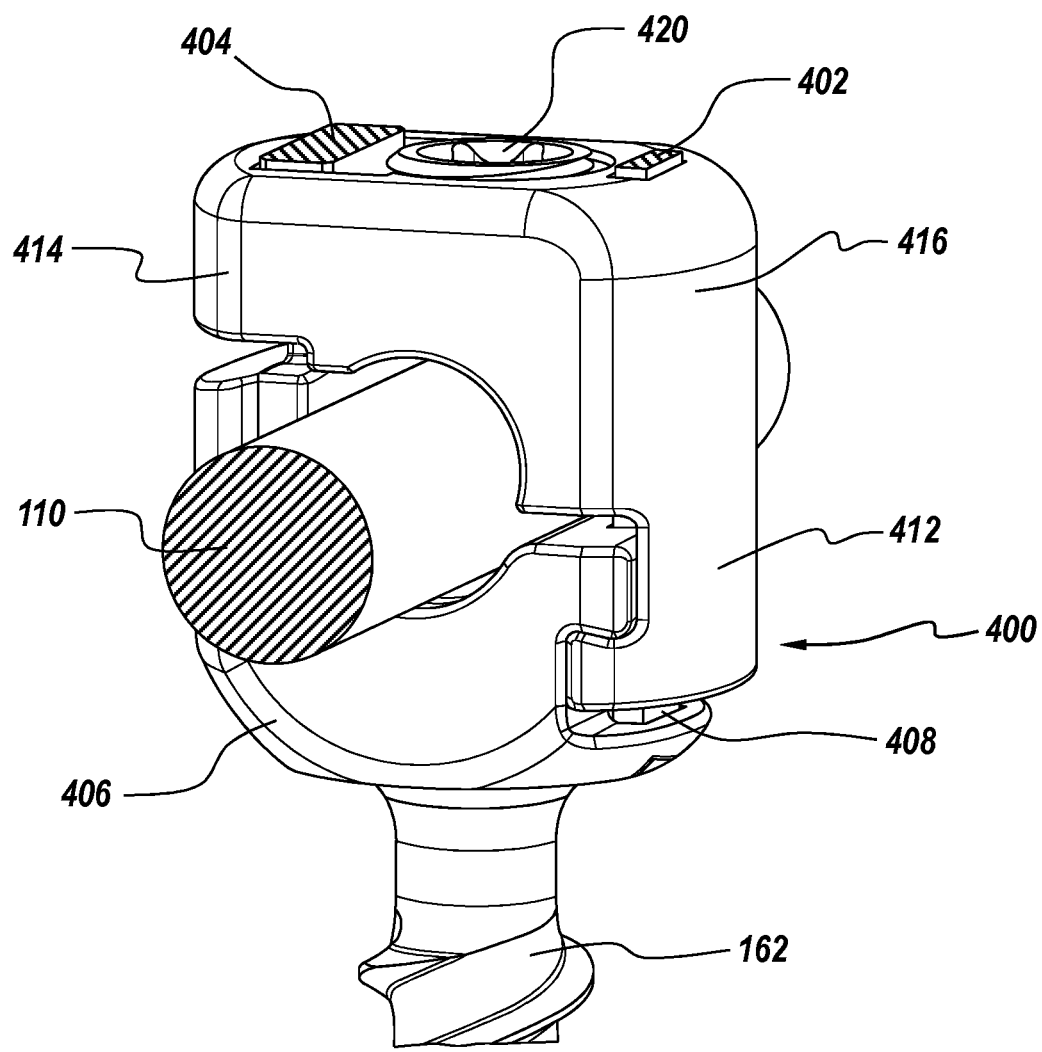

In the exemplary embodiment illustrated in FIGS. 2A-2E, the locking cap 316 is provided with a press fitting closure mechanism 250 for stabilizing the spinal fixation element 110 in place. The locking cap 316 is lowered along the flexible extension element 302 and the substantially rigid extension element 304 and locked in place by merely pressing on the locking cap 316. The side sections of the locking cap 316 couple to the side sections of the head plate 306. The locking cap 316 is snapped in place as illustrated in FIG. 2C. The spinal fixation element 110 may be securely held in place between the locking cap 316 and the head plate 306. As illustrated in FIG. 2B, the head plate 306 may include a saddle portion 308 that receives the spinal fixation element 110. The spinal fixation element 110 is positioned on the saddle 308 and locked in place using the press fitting closure mechanism 250. Alternatively, the press fitting closure mechanism 250 illustrated in FIGS. 2A-2E may be used with an exemplary embodiment where both elongated extension elements are flexible.

The locking cap 316 may also include a set screw 320. The set screw 320, when reduced within the locking cap 316, may press the spinal fixation element 110 onto the saddle 308. The exemplary embodiment illustrated in FIGS. 2A-2E may be used with a polyaxial screw where the head portion 160 of the screw 108 may be held within the head plate 306 and the shaft 162 of the screw 108 may rotate about a central axis of the head plate 306. When a polyaxial screw is used, the set screw 320 pressing the spinal fixation element 110 onto the saddle 308 may also lock the polyaxial screw so as to restrict the movement of the polyaxial screw within the head plate 306. According to various embodiments of the present invention, the exemplary embodiment illustrated in FIGS. 2A-2E may be used with a uni-screw.

FIGS. 3A-3E illustrate an exemplary spinal implant 300 including a dovetail closure mechanism 400 as another exemplary closure mechanism. In the exemplary embodiment illustrated in FIGS. 3A-3E, the exemplary spinal implant 300 is provided with a substantially rigid elongated extension element 404 and a flexible elongated extension element 402. According to various embodiments of the present invention, the elongated extension elements may be both rigid, both flexible or any combination thereof. Any of elongated extension elements 402 and 404 may be integrally formed with the head plate 406. Alternatively, the elongated extension elements 402 and 404 may be connected to the head plate 406 via a mechanical connection. According to various embodiments of the present invention, the flexible elongated extension element 402 and the substantially rigid elongated extension element 404 may be provided with surface features 122, such as those illustrated in FIG. 1A, to help reduce a locking cap 416 along the elongated extension elements 402 and 404.

The locking cap 416 may be placed over the substantially rigid elongated extension element 404 and the flexible elongated extension element 402. The locking cap 416 may have a longer side section 412 and a shorter side section 414. The longer side section 412 of the locking cap 416 fits over a shorter side section of the head plate 406. The shorter side section 414 of the locking cap 416 fits over a longer side section of the head plate 406 so as to form a dovetail closure mechanism 400. The longer side section 412 of the locking cap 416 has a tooth 422 that fits into a recess 408 formed on the head plate 406. The locking cap 416 is locked to the head plate 406 by pressing the tooth 422 into the recess 408. A saddle element 410 may be coupled to the head plate 406 to receive the spinal fixation element 110. The spinal fixation element 110 is positioned on the saddle 410 and locked in place using the dovetail closure mechanism 400.

In the exemplary embodiment illustrated in FIGS. 3A-3E, the locking cap 416 may also include a set screw 420. The set screw 420, when reduced within the locking cap 416, may press the spinal fixation element 110 onto the saddle 410. The exemplary embodiment illustrated in FIGS. 3A-3E may be used with a polyaxial screw where the head portion 160 of the screw 108 may be held within the head plate 406 and the shaft 162 of the screw 108 may rotate about a central axis of the head plate 406. When a polyaxial screw is used, the set screw 420 pressing the spinal fixation element 110 onto the saddle 410 may also lock the polyaxial screw so as to restrict the movement of the polyaxial screw within the head plate 406. According to various embodiments of the present invention, the exemplary embodiment illustrated in FIGS. 3A-3E may be used with a uni-screw.

Figure 4:
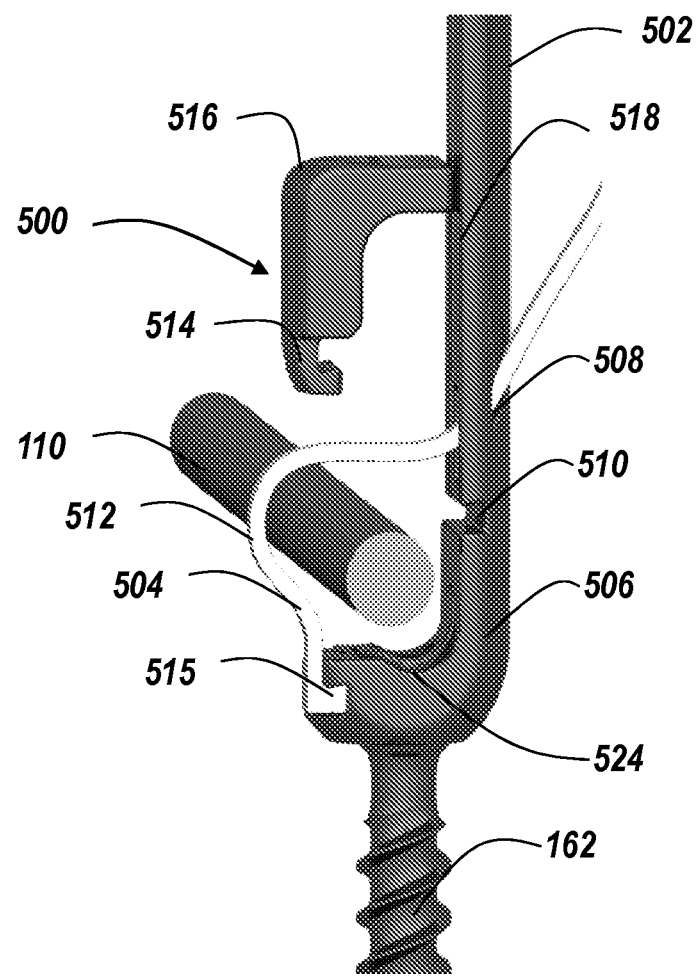
FIG. 4 illustrates an exemplary spinal implant with one flexible elongated extension element and a substantially rigid elongated extension element.

FIG. 4 illustrates an exemplary spinal implant 400 with a flexible elongated extension element 504 and a substantially rigid elongated extension element 502. The flexible elongated extension element 504 and the rigid elongated extension element 502 may be integrally formed with the head plate 506. Alternatively, the elongated extension elements 502 and 504 may be coupled to the head plate 506 via a mechanical connection. According to various embodiments of the present invention, the substantially rigid elongated extension element 502 and the flexible elongated extension element 504 may be provided with surface features 122, such as those illustrated in FIG. 1A, to help reduce a locking cap 516 along the elongated extension elements 502 and 504.

The flexible elongated extension element 504 may fit through an opening 508 provided on the substantially rigid elongated extension element 502 forming a loop 512 over the spinal fixation element 110. The opening 508 may include an engagement mechanism, such as a tooth, that engages the flexible elongated extension element 504 when the loop 512 is formed. The engagement mechanism may help to laterally reduce the spinal fixation element 110 when the flexible elongated extension element 504 is pulled manually or using an instrument through the opening 508. The loop 512 stabilizes the spinal fixation element 110 on a saddle portion 524 coupled to the head plate 506 and prevents a lateral translation of the spinal fixation element 110. The locking cap 516 may slide on a track 518 provided on the substantially rigid elongated extension element 502. The locking cap 516 is set in place when the locking cap 516 slides into the recess 510 formed on the substantially rigid elongated extension element 502. The locking cap 516 may fit over the loop 512 to further stabilize the spinal fixation element 110. The locking cap 516 may include a tooth portion 514 provided at a distal end thereof. The tooth 514 may slide into a recess 515 provided on the head plate 506. The spinal fixation element 110 is positioned on the saddle 516 and locked in place using the locking assembly 500. The locking cap 516 sliding into the bottom recess 510 and the tooth portion 514 sliding into the recess 515 may cause an extra portion of the flexible elongated extension element 504 extending beyond the substantially rigid elongated extension element 502 to detach from the head plate 506. An extra portion of the substantially rigid elongated extension element 502 may be detached from the head plate 506 by cutting or using a snap-off feature.

Figure 5:
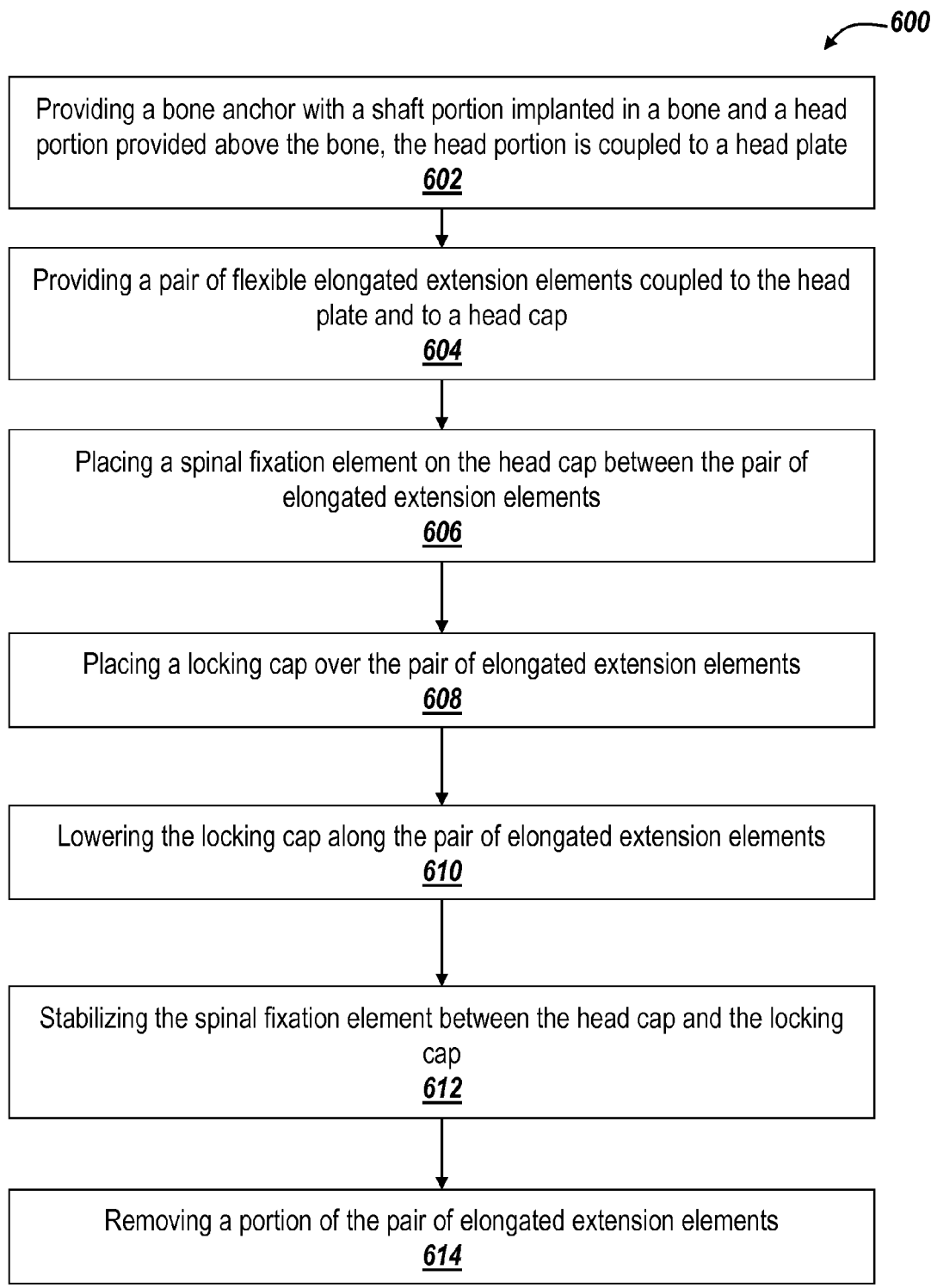
FIG. 5 is a flowchart of steps for positioning the spinal fixation element in the exemplary spinal implant with a pair of flexible elongated extension elements.

FIG. 5 is a flowchart of steps 600 for positioning the spinal fixation element in the exemplary spinal implant with a pair of flexible elongated extension elements. The exemplary spinal implant includes a bone anchor, e.g. a bone screw, with a shaft portion implanted in a bone and a head portion provided above the bone. The bone anchor is coupled to a head plate by passing though a central opening of the head plate (step 602). The exemplary bone anchor may be a poly-axial screw, a mono-axial screw and/or a uni-screw. A pair of flexible elongated extension elements is also coupled to the head plate by passing through openings provided on each side of the head plate (step 604). The pair of flexible elongated extension elements may be integrally formed with the head plate. Alternatively, the pair of flexible elongated extension elements may be formed as a monolithic element that is placed through the openings of the head plate so as to form two elongated extension elements. The pair of elongated extension elements is also coupled to a head cap. The elongated extension elements pass through the openings provided on each side of the head cap. The openings of the head cap may be aligned with the openings of the head plate. The head cap is provided on the head plate so as to compress the head plate and the head portion of the bone anchor. A spinal fixation element is placed on the head cap between the pair of elongated extension elements (step 606). A locking cap is placed over one or more elongated extension elements for locking the spinal fixation element in place between the locking cap and the head cap (step 608). The locking cap is lowered along one or more of the elongated extension elements (step 610). According to one exemplary embodiment, the pair of flexible elongated extension elements may be pulled away from each other to lower the locking cap along the pair of elongated extension elements. According to another exemplary embodiment, a set screw may be provided through the locking cap. The set screw may be threaded down to lower the locking cap along the pair of elongated extension elements toward the head cap. Once the locking cap is lowered toward the head cap, the spinal fixation element is stabilized between the head cap and the locking cap (step 612). Therefore, the spinal fixation element is securely held in place. A portion of the elongated extension elements may be provided above the skin incision at the surgery site. At the end of the surgery, the portion of the pair of elongated extension elements that stick out of the incision are easily removed by cutting or disengaging the elongated extension elements (step 614).

Figure 6:
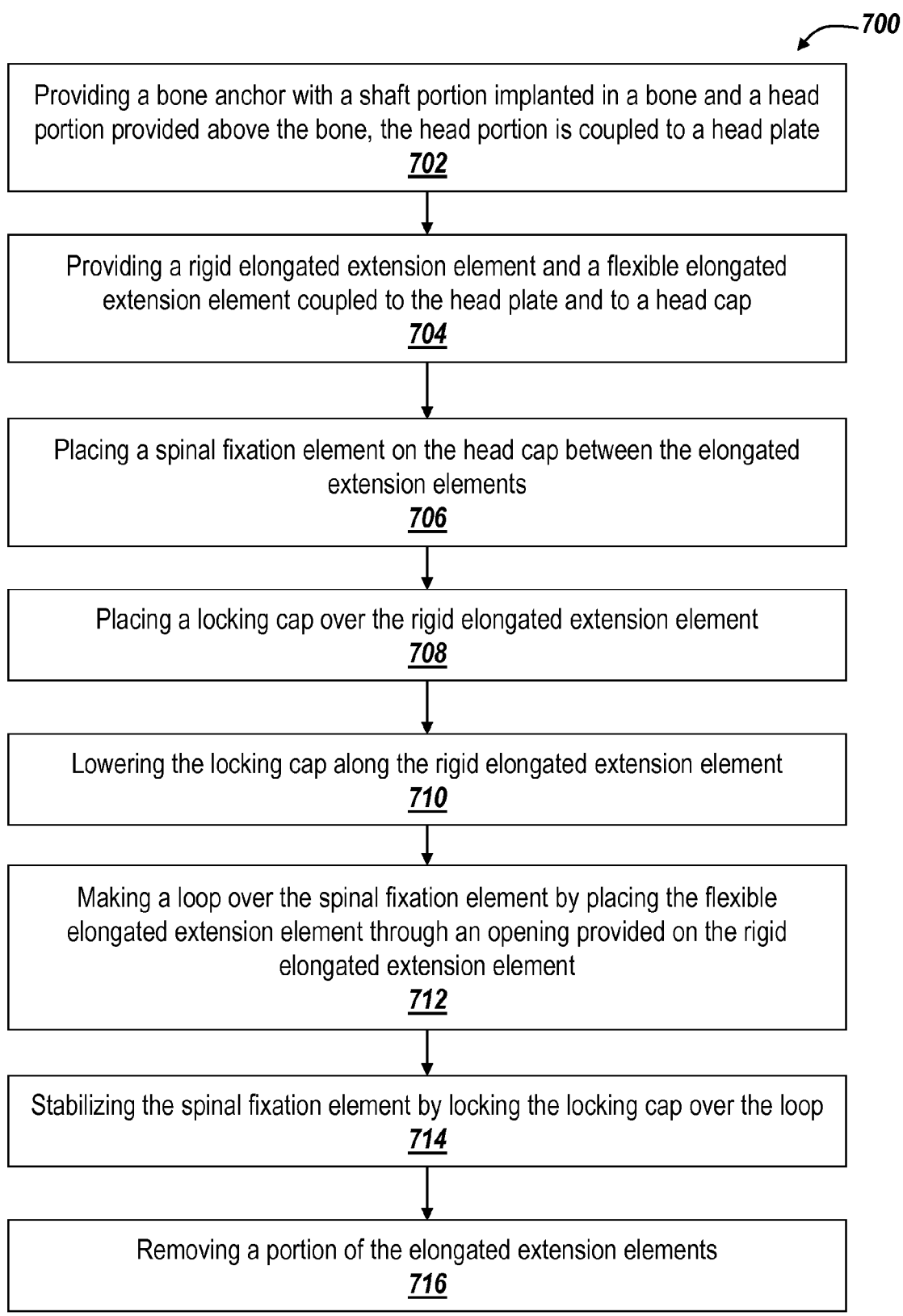
FIG. 6 is a flowchart of steps for positioning the spinal fixation element in the exemplary spinal implant with one flexible elongated extension element and one rigid elongated extension element.

FIG. 6 is a flowchart of steps 700 for positioning the spinal fixation element in the exemplary spinal implant with one flexible elongated extension element and one rigid elongated extension element. The exemplary spinal implant includes a bone anchor with a shaft portion implanted in a bone and a head portion provided above the bone. The bone anchor is coupled to a head plate by passing though a central opening of the head plate (step 702). A rigid elongated extension element and a flexible elongated extension element are also coupled to the head plate (step 704). The pair of elongated extension elements may be integrally formed with the head plate. Alternatively, the pair of flexible elongated extension elements may be coupled to the head plate by passing through the openings provided on each side of the head plate. The elongated extension elements also coupled to a head cap by passing through the openings provided on each side of the head cap. The openings of the head plate may be aligned with the openings of the head cap. The head cap is provided on the head plate so as to compress the head plate and the head portion of the bone anchor. A spinal fixation element is placed on the head cap between the elongated extension elements (step 706). A locking cap is placed over the rigid elongated extension element for locking the spinal fixation element in place (step 708). The locking cap is lowered along the rigid elongated extension element toward the head cap (step 710). The locking cap is provided to stabilize the spinal fixation element in place. According to an exemplary embodiment, it is possible to further stabilize the spinal fixation element in place by making a loop over the spinal fixation element by placing the flexible elongated extension element through an opening provided on the rigid elongated extension element (step 712). Then the locking cap may be locked in placed over the loop, stabilizing the spinal fixation element in place (step 714). Therefore, the spinal fixation element is securely held in place between the locking cap and the head cap. A portion of the elongated extension elements may be provided above the skin incision at the surgery site. At the end of the surgery, the portion of the pair of elongated extension elements that stick out of the incision are easily removed by cutting or disengaging the elongated extension elements from the head portion (step 716).

According to various embodiments of the present invention, the pair of elongated elements may have a biased distal geometry. The biased distal geometry may have a larger opening than a surface of the head plate of the spinal implant. The biased distal geometry allows for the horizontal movement of the spinal fixation element.

The flexible elongated extension elements described herein may be constructed of any biocompatible material including, for example, plastic, nitinol to allow for a biased geometry to allow vertebral correction and easier placement of the spinal fixation element. The rigid elongated extension elements described herein may be constructed of metal, such as titanium, stainless steel, polymers, ceramics, or composites thereof.

The present invention is described above relative to certain exemplary embodiments to provide an overall understanding of the principles of the structure, function, manufacture, and use of the spinal implant disclosed herein. Those skilled in the art will appreciate that the present invention may be implemented in a number of different applications and embodiments and is not specifically limited in its application to the particular embodiments depicted herein.

A person having ordinary skill in the art will appreciate that the aforementioned methods and implants can be modified depending on the type of anchor being used, as well as the specific procedure being employed. Moreover, other methods and devices known in the art can be used in accordance with the present invention.

One skilled in the art will appreciate further features and advantages of the invention based on the above-described embodiments. Accordingly, the invention is not to be limited by what has been particularly shown and described, except as indicated by the appended claims.

While the instruments and methods disclosed herein have been particularly shown and described with reference to the exemplary embodiments thereof, those of ordinary skill in the art will understand that various changes may be made in the form and details herein without departing from the spirit and overall scope. Those of ordinary skill in the art will recognize or be able to ascertain many equivalents to the exemplary embodiments described specifically herein by using no more than routine experimentation. Such equivalents are intended to be encompassed by the overall scope and the appended claims.

The invention claimed is:

1. A spinal implant comprising:
a bone anchor having a head portion and a shaft extending along a longitudinal axis of the bone anchor configured to engage a bone;
a head plate coupled to the bone anchor, the head plate including:
a first elongated extension element provided on a first side of the head plate, wherein the first elongated extension element is flexible; and
a second elongated extension element provided on a second side across from the first side of the head plate; and
a head cap coupled to the head plate, the first elongated extension element and the second elongated extension element, wherein:
the head plate comprises a pair of openings provided at each side thereof,
the head cap comprises a pair of openings provided at each side thereof,
the first elongated extension element passes through a first opening of the head plate and a first opening of the head cap, the first opening of the head plate is aligned with the first opening of the head cap, and
the second elongated extension element passes through a second opening of the head plate and a second opening of the head cap, the second opening of the head plate is aligned with the second opening of the head cap,
wherein the spinal implant is configured to receive a spinal fixation element on a seat portion of the head cap provided between the first elongated extension element and the second elongated extension element,
an anchor locking cap adapted to move along at least one of the first elongated extension element and the second elongated extension element, wherein the anchor locking cap is adapted to fit over the spinal fixation element placed between the seat portion of the head cap and the anchor locking cap, and a plurality of reduction features provided on at least one of the first elongated extension element and the second elongated extension element to provide a controlled movement of the anchor locking cap along at least one of the first elongated extension element and the second elongated extension element, the controlled movement preventing the anchor locking cap from sliding along the first elongated extension element or the second elongated extension element.

2. A spinal implant comprising:

a bone anchor having a head portion and a shaft extending along a longitudinal axis of the bone anchor configured to engage a bone;

a head plate coupled to the bone anchor, the head plate including:
- a first elongated extension element provided on a first side of the head plate, wherein the first elongated extension element is flexible; and
- a second elongated extension element provided on a second side across from the first side of the head plate; and a head cap coupled to the head plate, the first elongated extension element and the second elongated extension element, wherein:

the head plate comprises a pair of openings provided at each side thereof, the head cap comprises a pair of openings provided at each side thereof, the first elongated extension element passes through a first opening of the head plate and a first opening of the head cap, the first opening of the head plate is aligned with the first opening of the head cap, the second elongated extension element passes through a second opening of the head plate and a second opening of the head cap, the second opening of the head plate is aligned with the second opening of the head cap, and wherein the spinal implant is configured to receive a spinal fixation element on a seat portion of the head cap provided between the first elongated extension element and the second elongated extension element, an anchor locking cap adapted to move along at least one of the first elongated extension element and the second elongated extension element, wherein the anchor locking cap is adapted to fit over the spinal fixation element placed between the seat portion of the head cap and the anchor locking cap, and a set screw for locking the anchor locking cap in place to prevent the anchor locking cap from moving along at least one of the first elongated extension element and the second extension element.

* * * * *